United States Patent [19]

Obenchain

[11] Patent Number: 5,313,962
[45] Date of Patent: May 24, 1994

[54] METHOD OF PERFORMING LAPAROSCOPIC LUMBAR DISCECTOMY

[76] Inventor: Theodore G. Obenchain, 12002 Royal Birkdale Row, #A, San Diego, Calif. 92128

[21] Appl. No.: 24,517

[22] Filed: Mar. 1, 1993

Related U.S. Application Data

[63] Continuation-in-part of Ser. No. 780,865, Oct. 18, 1991.

[51] Int. Cl.$^5$ .............................................. A61B 17/36
[52] U.S. Cl. ........................................ 128/898; 606/1; 606/14
[58] Field of Search .................. 128/898, 747, 4, 6, 128/362, 395, 397, 398; 606/15, 16, 13, 14, 45, 46

[56] References Cited

U.S. PATENT DOCUMENTS

| | | | |
|---|---|---|---|
| 4,122,853 | 10/1978 | Smith . | |
| 4,545,374 | 10/1985 | Jacobson | 606/61 |
| 4,573,448 | 3/1986 | Kambin | 128/898 |
| 4,583,539 | 4/1986 | Karlin et al. . | |
| 4,638,799 | 1/1987 | Moore | 606/1 |
| 4,678,459 | 7/1987 | Onik et al. | 604/22 |
| 4,863,477 | 9/1989 | Monson | 623/17 |
| 4,984,563 | 1/1991 | Renaud . | |
| 4,998,527 | 3/1991 | Meyer . | |
| 5,027,792 | 7/1991 | Meyer . | |
| 5,084,043 | 1/1992 | Hertzmann et al. | 606/13 |
| 5,100,420 | 3/1992 | Green et al. | 128/4 |
| 5,131,382 | 7/1992 | Meyer | 604/22 |

OTHER PUBLICATIONS

Burton, "Surgical Diskectomy 1991: Status Report", Seminars in Orthopedics, vol. 16, No. 2, Jun. 1991, pp. 92-97.

Obenchain, "Journal of Laparoendoscopic Surgery", Laparoscopic Lumbar Discectomy: Case Report, vol. 1, No. 3, 1991 pp. 145-149.

Primary Examiner—Stephen C. Pellegrino
Assistant Examiner—Jeffery A. Schmidt
Attorney, Agent, or Firm—Jerry R. Seiler

[57] ABSTRACT

In one method for performing a laparoscopic lumbar discectomy an incision is created in the abdominal wall of a patient. The peritoneal lining is dissected from the abdominal wall while relocating the peritoneal lining toward the midline of the abdomen to create an expanded retroperitoneal space. A surgical apparatus is inserted into the incision comprising an endoscope and surgical means suitable for performing a lumbar discectomy. The surgical apparatus is directed through the expanded retroperitoneal space until the surgical apparatus approaches the anterior aspect of a vertebral body and a discectomy is performed on the vertebral body.

17 Claims, 4 Drawing Sheets

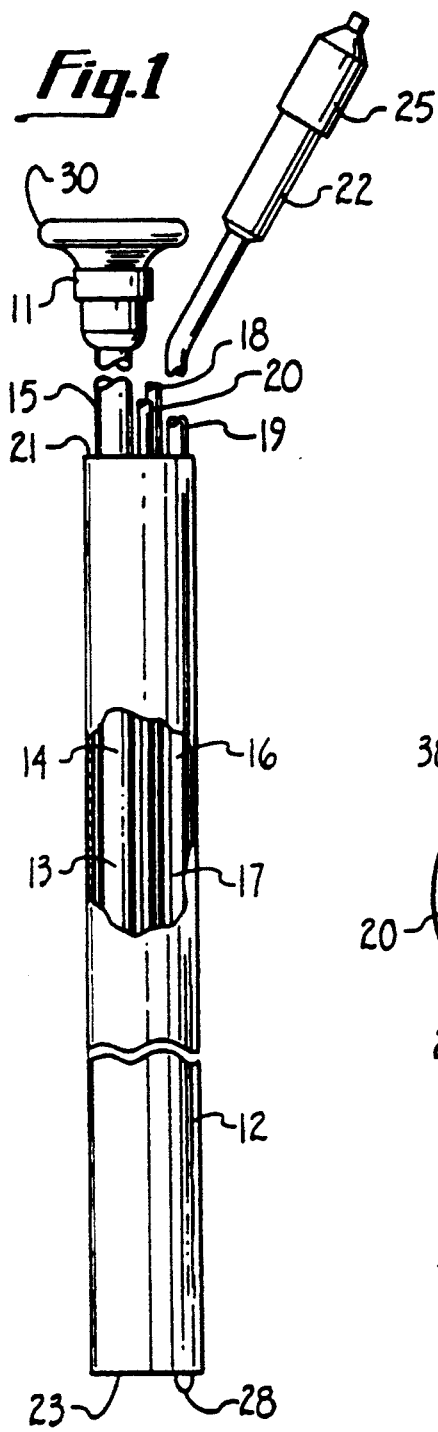
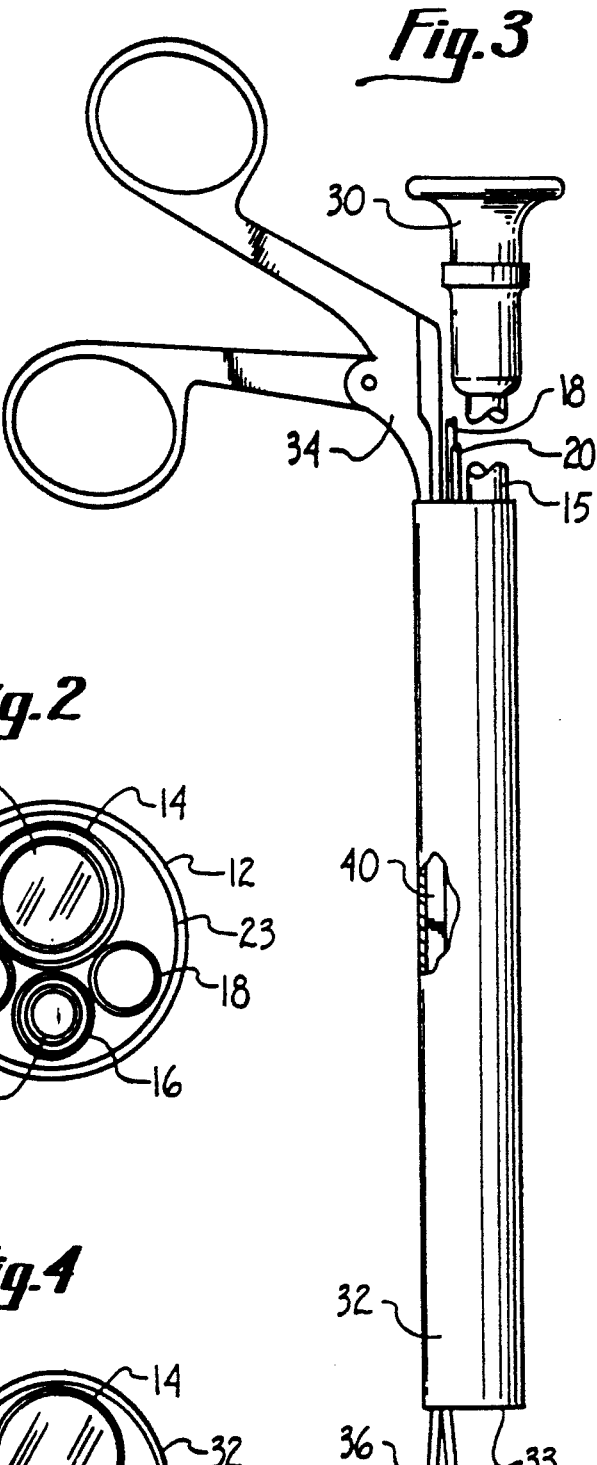
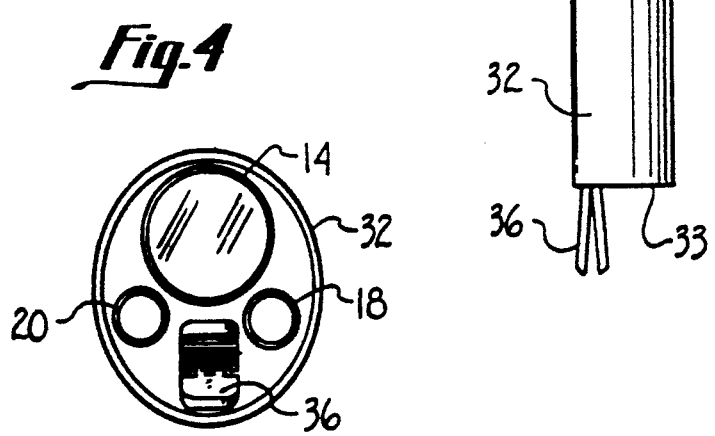

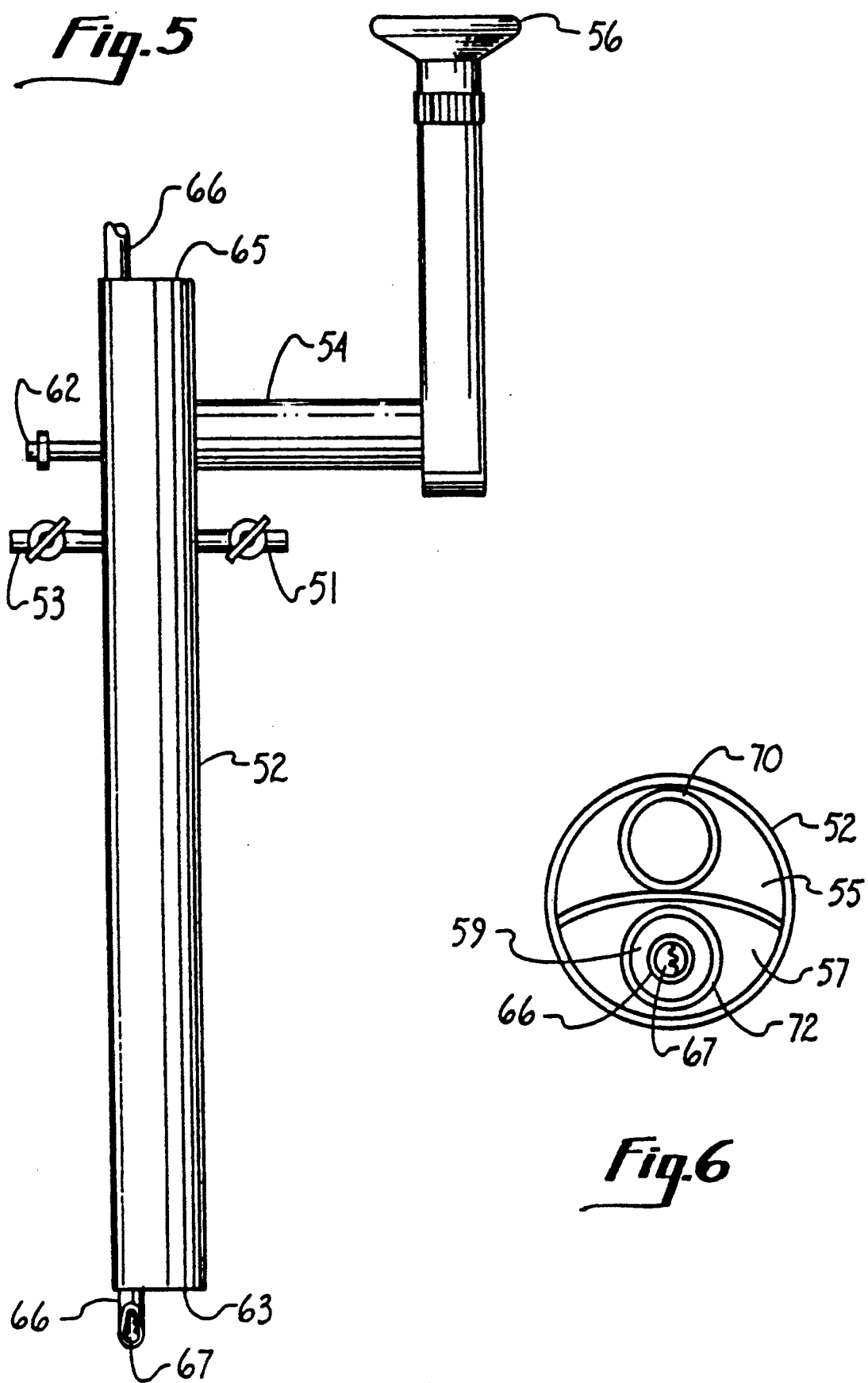

METHOD OF PERFORMING LAPAROSCOPIC LUMBAR DISCECTOMY

BACKGROUND OF THE INVENTION

This application is a continuation-in-part of application number 07/780,865 to Obenchain, filed Oct. 18, 1991, the entire contents of Which is hereby incorporated by reference.

Lumbar surgery to remove discs or portions of discs which have herniated has heretofore generally involved posterior entry. More recently, surgery using both endoscopic observation and control and a laser fiber instrument for incising the annulus and removing disc tissue has involved entry from one or two different posterior angles. Using such a technique, the endoscope is viewed from one angle, while the laser surgical tool or other surgical instrument is directed and guided during the surgery from a different angle. Such a procedure requires two spinal punctures into the patient thereby doubling the risk of nerve root injury. It is to the elimination of a dual puncture surgery for lumbar discectomy and to improve the control and observation of a lumbar discectomy utilizing a single disc entry while the patient is in a supine position that the present invention is directed. Although endoscopic surgical devices are known, such devices comprise elongated surgical forceps having a built-in tube for receiving an endoscope. However, such devices do not provide an endoscopic tool having a feature which allows insertion and removal of different selected surgical instruments during the surgery while the device itself remains in the abdominal cavity.

Posterior entry for lumbar discectomy has a number of complications such as the development of epidural scar tissue, the manipulation of neural structures and the removal of bone. Therefore, an anterior method for lumbar discectomy is disclosed which provides a more conservative approach to such surgery.

SUMMARY OF THE INVENTION

This invention provides improved methods for performing lumbar discectomies. Laparoscopic lumbar discectomies reduce both the size and number of incisions required and minimize postoperative trauma while speeding recovery.

In a first preferred embodiment of this invention, a method of performing a laparoscopic lumbar discectomy comprises creating one or more incisions through the abdominal wall and into the preperitoneal space of a patient, inserting surgical apparatus comprising an endoscope, dissecting means suitable for separating the peritoneal lining from the abdominal wall in both the preperitoneal and retroperitoneal space, and surgical means suitable for performing a lumbar discectomy. The method further comprises instilling a pharmaceutically acceptable gas into the preperitoneal and retroperitoneal space, thereby expanding the space, and dissecting the peritoneal lining from the abdominal wall while relocating the peritoneal lining toward the midline of the abdomen. After the transperitoneal space has been suitably expanded the discectomy apparatus of the invention is inserted through the space approaching the anterior aspect of a vertebral body and thereafter the discectomy is performed on the vertebral body. Preferably the incision is created through the abdominal wall and into the preperitoneal space and is preferably lateral to the abdominal midline. Still more preferably, the incision is adjacent the abdominal midline.

In another preferred embodiment of this invention a method is provided for performing a laparoscopic lumbar discectomy comprising inserting a surgical apparatus through an abdominal incision into the preperitoneal space. The surgical apparatus comprises an elongated sleeve member having a first and a second end, endoscope receiving means and an endoscope secured therein, laser fiber receiving means having a laser fiber secured therein, suction and irrigation channel means, and dissecting means for separating the peritoneal lining from the abdominal wall, each of the means extending along the interior of the sleeve member between the first and second end through the abdominal incision. The method of this embodiment further comprises directing the sleeve member into the preperitoneal space, observing the direction of the sleeve using the endoscope, guiding the sleeve member through the preperitoneal space and into the retroperitoneal space while separating the peritoneal lining from the abdominal wall using the dissecting means until the second end thereof is adjacent the exterior annulus of a vertebral disc space, surgically entering the disc space and removing disc tissue by energizing and manipulating the laser fiber, directing irrigating fluid through one or more of the conduits and removing fluid with suctioning through one or more of the conduits. It is also contemplated that the method additionally include the step of instilling a pharmaceutically acceptable gas into the preperitoneal and retroperitoneal space. Preferably the abdominal incision is lateral to the abdominal midline. In one preferred embodiment, the pharmaceutically acceptable gas is $CO_2$ and in another preferred embodiment, the pharmaceutically acceptable gas is air.

In yet another preferred embodiment of this invention a method is provided for performing a laparoscopic lumbar discectomy on a patient comprising creating an incision through the abdominal wall and into the preperitoneal space, creating a retroperitoneal space, inserting a surgical apparatus comprising an endoscope, irrigation and suction means, and means suitable for performing a lumbar discectomy, traversing the preperitoneal space and retroperitoneal space toward a lumbar vertebral body with the surgical apparatus until the surgical apparatus approaches the anterior aspect of the vertebral body, entering the disk space of the vertebral body, and performing the discectomy. Preferably the abdominal incision is lateral to the abdominal midline and more preferably the incision is adjacent the abdominal midline.

In another preferred embodiment of this invention, a method is provided for performing a laparoscopic lumbar discectomy on a patient comprising creating an incision in the abdominal wall of a patient, instilling a pharmaceutically acceptable gas to expand the retroperitoneal region located between the incision and the lumbar vertebrae, without disecting the peritoneum, inserting a surgical apparatus comprising an endoscope and surgical means for performing a lumbar discectomy into the incision, directing the surgical apparatus through the regions and performing the discectomy on at least one vertebral body. Preferably the incision is adjacent the abdominal midline. In one embodiment the pharmaceutically acceptable gas is $CO_2$ and in another preferred embodiment, the pharmaceutically acceptable gas is air.

BRIEF DESCRIPTION OF THE DRAWINGS

FIG. 1 is a side view, partially broken away, illustrating the apparatus of the invention comprising an endoscope and fiber laser tool received therein;

FIG. 2 is an end view of the apparatus of FIG 1;

FIG. 3 is a side view of another embodiment of the invention showing a device having a rongeur surgical instrument received therein;

FIG. 4 is an end view of the apparatus of FIG 3;

FIG. 5 is a side view of another embodiment having a 90° endoscopic elbow, and light source port and mounting components;

FIG. 6 is an end view of the device of FIG. 5;

DETAILED DESCRIPTION OF THE INVENTION

Figure 7:
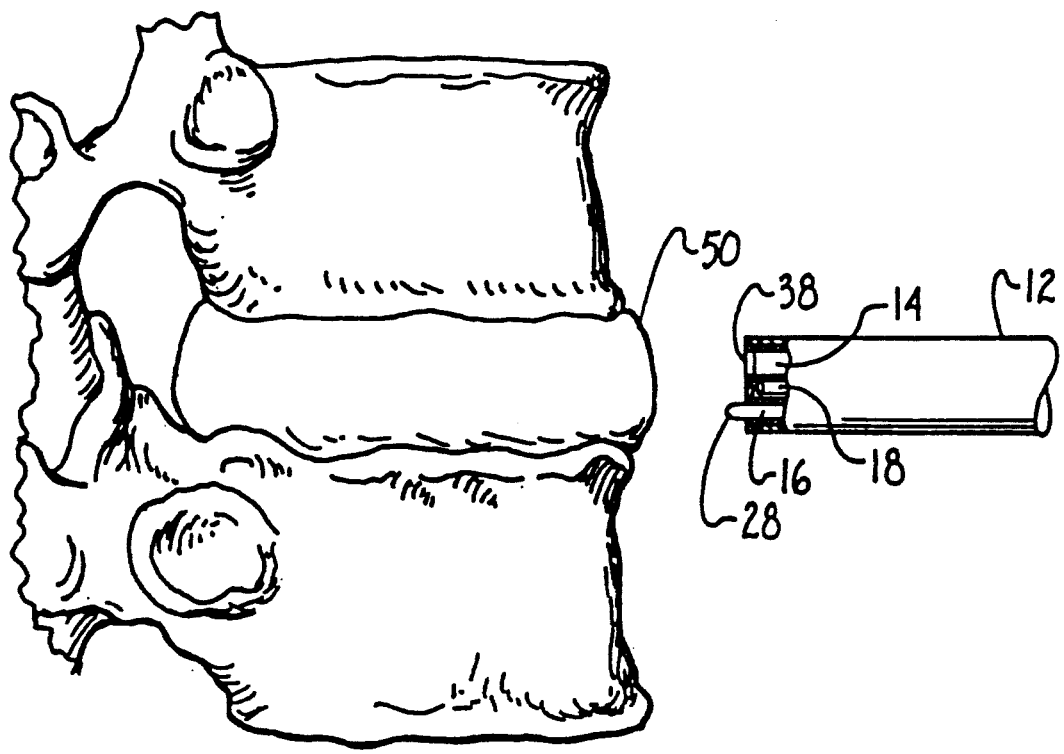
FIG. 7 illustrates a method of using the apparatus of FIG. 1 for laparoscopic lumbar discectomy.

Referring to FIGS. 1 and 2, there is illustrated a first embodiment of the apparatus of the invention having an endoscope and a fiber laser device received and secured therein. The specific components of the apparatus include a sleeve member 12 comprising an elongated cylinder having a first end 21 and a second end 23. The sleeve may be any desired shape, preferably round or oval, and having a relatively smooth exterior surface, without sharp edges or corners. The relative size of the sleeve is important. The length between the first and second ends must be sufficient to allow the surgeon or user to insert the device into a cavity of a patient, with the second end 23 adjacent the specific site of the surgery being carried out, and with the outer or first end 21 extending outwardly of the patient's cavity. For example, in abdominal or thoracic surgery, sleeve 12 must be a length of between about 15 and about 38 cm. However, it will be understood that different lengths for different specific uses may be used, and the criticality of the length will primarily be defined by the surgical procedure for which the device is to be used.

The cross-sectional outer diameter dimensions are also important, and must be large enough to accommodate the interior conduits, tubes, pipes, and other components, and yet be small enough to allow insertion into a relatively small incision, obviously preferable to minimize trauma. It has been found that a sleeve having a maximum exterior cross-sectional dimension of about 10 mm, and preferably between about 5 or about 9 mm is quite suitable for lumbar discectomy and many other procedures.

Interiorly of the sleeve 12 are secured an endoscope receiving means comprising a channel member 14 extending substantially entirely along the interior length of the sleeve between ends 21 and 23. Channel member 14 includes an interior portion 13, and an exterior portion 15 terminating in an adaptor or fitting 11 for receiving eyepiece 30 of an endoscope. The fitting may threadedly engage the endoscope for securing it in place, or it may simply otherwise allow the endoscope eyepiece to be nested in its proper position for use during surgery. In either event, the endoscope must be rotatable in the apparatus, to enable the user to rotate the endoscope to view the surgical site from any angle. The endoscope receiving channel or tube must also be of a shape to adequately receive and hold the elongated endoscope in place in the apparatus, as well as to provide positioning of the lens 38 substantially coterminous with the end 23 of sleeve 12. The channel also allows the user to conveniently grasp adaptor and/or eyepiece 30 for rotating the endoscope eyepiece to observe the surgical site as well as to direct the apparatus through an incision and into the cavity where the surgery is performed.

A second channel member 16 is provided and secured in sleeve 12 for receiving and directing a laser fiber therealong. As shown, a laser fiber device having a handle member 25 and a laser emitter 28 at the opposite end is received and secured in channel member 16 having an interior portion 17 extending between ends 21 and 23 of sleeve 12 and an exterior portion 19 terminating in a fitting or adaptor 22 for securing the laser handle member 25. The laser fiber receiving means must be of sufficient length to allow the emitter 28 to be positioned properly adjacent sleeve end 23 when the fiber laser device is secured. It will be understood to those skilled in the art that different types of fiber lasers may be used and accommodated in the apparatus of the invention, including a free beam laser, such as $CO_2$, or a contact fiber laser, such as a Holmium or Nd:YAG type. Where a free beam laser is used, the fiber laser emitter 28 will usually extend beyond end 23 of sleeve 12 as illustrated in FIG. 1, while in the latter case, the fiber laser emitter may be coterminous with the sleeve end. Any suitable type of adaptor or fitting member 22 for securing the fiber laser surgical tool in the apparatus may be incorporated.

A plurality of conduits 18 and 20 to provide irrigation of the surgical site and to suction tissue and fluid to be removed from the site are provided by conduits 18 and 20. Any number of such irrigation and suction conduits may be installed in the device, depending on the type of surgery and needs of the surgeon and techniques or procedures in which the apparatus is to be used. The conduits may extend parallel adjacent the channel members as shown, or may be concentrically arranged as will be described hereinafter. The conduits preferably extend outwardly beyond first end 21 of sleeve 12, as shown, to provide means for being secured to hoses or pipes for directing irrigating fluid into the surgical site and removal of the fluid material therefrom. The length of the fluid handling conduits provides ports coterminous with a second end 23 of sleeve 12 and the conduits are secured and extend substantially along the interior length of the sleeve 12 as illustrated.

In FIGS. 3 and 4, there is illustrated another embodiment of the invention, also comprising a device having an endoscope securing feature as previously described, together with a plurality of fluid handling conduits for irrigating and suctioning the surgical site. In this embodiment, an alternative shape for sleeve 32 is illustrated, and is observed in FIG. 4 as being oval or oblong in cross-sectional shape. The device includes channel member 40 for receiving one or more of a plurality of different conventional surgical instruments. A conventional rongeur 34 is shown having blades 36 which may be actuated by the surgeon for cutting and removing bone or tissue. Although a rongeur is illustrated as being received in the device, it may be removed and other types of conventional surgical tools such as, for example, a free beam laser or a shaver, which may extend for some length beyond sleeve end 65 and substantially along the sleeve axis, and inserted, for example a trephine, curette, shaver or a trocar or other similar surgical tools, well known to those skilled in the art. Thus, any one of these surgical instruments may be conveniently inserted in the device and guided and manipulated by the surgeon having endoscopic observation for directing the apparatus through a patient's cavity to the surgical site and for manipulating and controlling the instrument. During the surgery, different surgical instruments may be selected by the surgeon and received in and removed from elongated channel 40 as the procedure dictates, with irrigation and suction being performed via fluid handling channels 18 and 20 and endoscopic observation and monitoring of the procedure provided using endoscope 30. Although both embodiments shown in FIGS. 1–4 illustrate the use of an eyepiece 30 on the endoscope, it will be understood that the endoscope will usually be attached to a video camera having projection means so that the surgeon may view and control the surgery by observing a conveniently located video screen.

Another embodiment of the apparatus of the invention is shown in FIGS. 5 and 6. In the embodiment shown, sleeve 52 is provided with an elbow 54 which extends out of the way of the plane and axis of the sleeve so that substantially straight cutting or surgical tools can be used without interfering with the observation of the surgery using an endoscope or attachment for a video camera. In such an embodiment, a 90° elbow 54 extends from the sleeve and is provided with an attachment device 56 for securing a video camera, or the like. Although the endoscopic 90° elbow is shown, a straight or angled attachment may be used for the same purpose, so long as it provides for endoscopic, video or other observation away from the axis of the sleeve to allow the surgeon to conveniently manipulate the tool extending from the sleeve. In addition, in the embodiment illustrated, fittings 51 and 53 for attaching irrigation and suction components are also provided, as is a light source attachment component 62. In this embodiment, a straight shaver apparatus 66 having a cutting end which can be extended outwardly up to a few centimeters from the end 63 of the sleeve is provided. Shaver 66 illustrated includes a port 67 and a hollow interior communicating with a suction port (not shown) for directing tissue suctioned from the surgical site through port 67, along the hollow shaver interior and out through a suction port attached to a power source handle, (not shown), and well understood by those skilled in the art.

Observing also FIG. 6, the sleeve of this embodiment may include one or more irrigation and/or suction conduits 55, 57 and 59 for introducing irrigating fluids and/or removing the tissue from the surgical site. If the device of the invention is to be used with a hollow shaver or other hollow surgical device through which tissue can be suctioned, a single port or multiple irrigation ports for directing irrigation fluid to the surgical site may be used. Where the surgical tool, for example a free beam laser, is to be used, both irrigation and suctioning the conduits are provided in the sleeve apparatus of the invention. As illustrated, the shape of such channels is not critical and, for example, one or more annular conduits 59 concentrically located around the surgical instrument may be incorporated, or other shaped channels may be conveniently formed along the sleeve interior adjacent the guide channels 70 and 72 for the endoscope and surgical tool.

Figure 8:
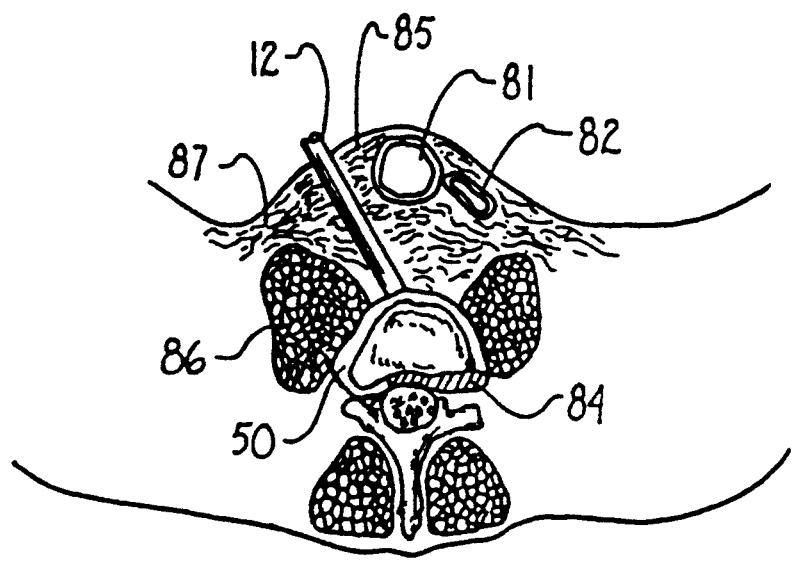
FIG. 8 further illustrates a method of performing surgery according to the invention.

FIGS. 7 and 8 schematically illustrates the use of the apparatus of FIG. 1 in a laparoscopic lumbar discectomy procedure of the invention which is believed to offer substantial advantages over state of the art lumbar discectomy procedures. In such a procedure, the patient is placed in a supine or lithotomy position, and the abdomen preferably distended with air or carbon dioxide ($CO_2$). The surgeon observes the procedure preferably using a video camera attached to the endoscope and viewing the video screen. The surgeon directs the apparatus of the invention, including the cutting tool inserted in the appropriate channel of sleeve 12, through an abdominal incision, for example, immediately above the pubic bone. Direction is continued through soft tissue, which may be teased, coagulated or vaporized using the laser or other surgical tool until it is adjacent the exterior of the disc space annulus 50. Surgery carried out between lumbar vertebrae L3–4 and L4–5 may be accomplished by directing the sleeve 12 to the left of aorta 81 and inferior vena cava 82, between the aorta and the psoas muscle 86, and through the posterior peritoneum 87 and fatty tissue 85. If desired, the surgery may traverse through the psoas muscle. Where the surgery site is between L5 and S-1, the dissection is preferably generally close to the midline between the iliac branches of the great vessels. Alternatively, for example, where the patient has extensive abdominal adhesions, it may be preferred to use a lateral puncture of the abdomen to avoid bowel perforation, and entry into the disc space is lateral, transversing the psoas muscle, or immediately in front of it. Once the apparatus reaches the exterior of the disc space annulus or ligament, a trephine may be used to penetrate the annulus and traverse the disc space, again using endoscopic and fluoroscopic control and guidance, and then proceed with the discectomy for removing herniated disc material 84. A fiber laser emitter 28 or other surgical device for cutting and removing bone and disc tissue is illustrated in FIG. 7. It is to be understood that the surgery or portion of the surgery may be conducted by utilizing any one or more different surgical instruments selected and alternately inserted and removed from sleeve 16. Concurrently with the cutting and removal of tissue, fluid is introduced into one or more of the channels for irrigating the surgical site, and suction is applied to one or more of the other conduits or through a shaver or other hollow cutting instrument for removing the fluid and tissue cut and loosened by the surgery. After the discectomy is complete, the surgeon removes the apparatus, applies appropriate sutures, and closes the wound incision in the abdomen. Conventional surgical techniques used as part of such a procedure are known to those skilled in the art. The improved laparoscopic lumbar discectomy of the invention avoids posterior dual puncture techniques used heretofore and may be accomplished in an outpatient setting with a minimum use of oral narcotics.

Figure 9:
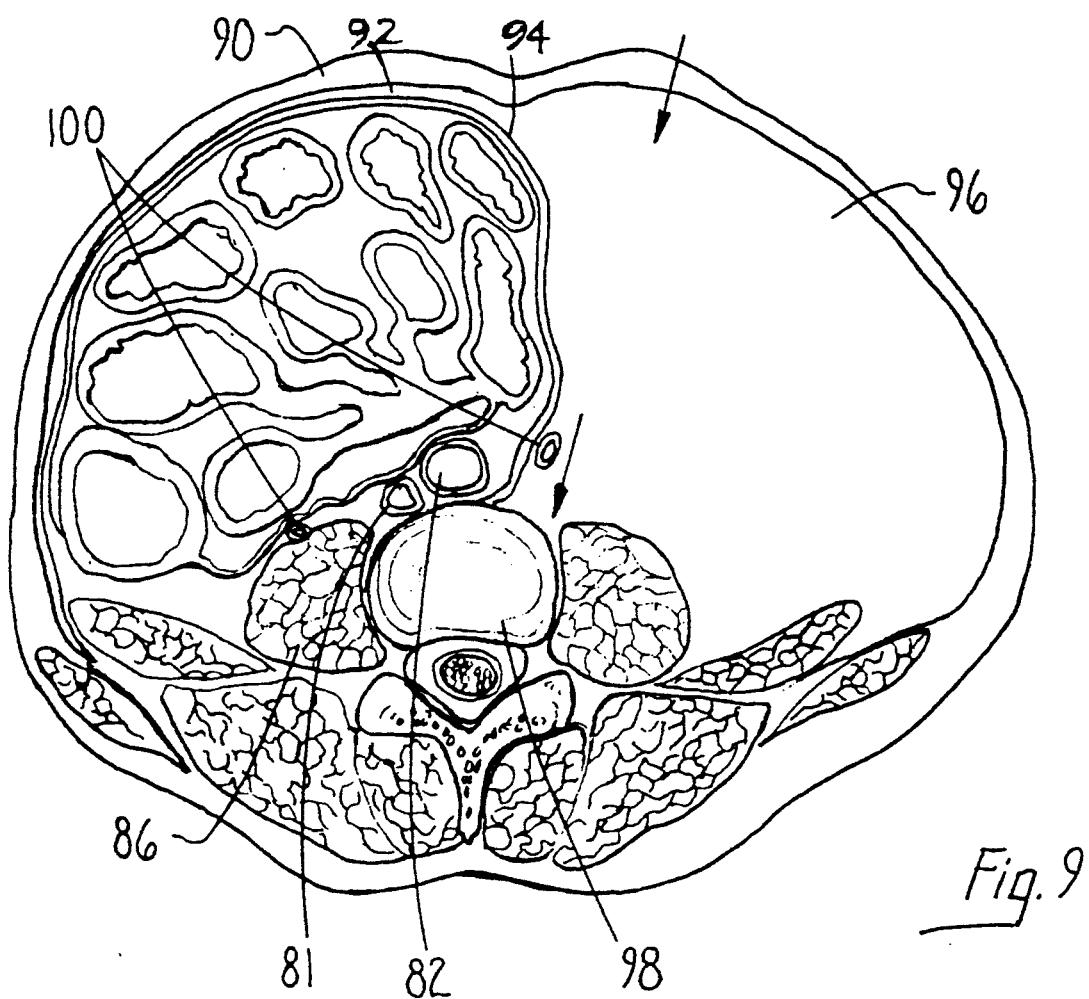
FIG. 9 illustrates another preferred method of performing a laparoscopic lumbar discectomy.

In another preferred surgical method using the laparoscopic lumbar discectomy technique of this invention, the lumbar discectomy procedure is performed by using a retroperitoneal technique in which the peritoneum remains intact. Like the transperitoneal approach disclosed above, the retroperitoneal approach is suitable for discectomy procedures involving any of the lumbar vertebrae. As an exemplary illustration, FIG. 9 provides a transverse section of the abdomen at approximately the L5 vertebral level.

Using the retroperitoneal method in a lumbar discectomy according to the invention, the patient is positioned in the supine or lithotomy position. While it is contemplated that the incision site for entry of the apparatus shown in FIGS. 1-6 can be located anywhere along the abdomen surface, the incision is preferably made below the epigastric and hypochondriac regions of the abdomen and is preferably lateral, that is, to the right or left of the abdominal midline. More preferably, the incision is directly adjacent the abdominal midline. For purposes of this application, the abdominal midline is a spatially defined line extending from the sternum through the umbilicus to the center of the pubic bone. As understood to those skilled in the art, laparoscopic trocars are punctured through the abdominal wall for insertion of multiple instruments for dissection and exposure of the front of the spine.

The retroperitoneal lumbar discectomy technique is particularly well-suited for discectomies involving the L3-4 and L4-5 vertebral spaces as well as L5-S1 spaces. Referring to FIG. 9, the abdominal incision continues through the abdominal wall 90 through the muscle and connective tissue and into the preperitoneal space 92. Care is taken to maintain the integrity of the peritoneal lining 94. Dissection is continued along the inner surface of the abdominal wall, separating the peritoneal lining from the preperitoneal and retroperitoneal space 96 while guiding the peritoneum toward the abdominal midline. Instruments typically required during this portion of the procedure include blunt dissecting tools, bowel retractor, endoscope and discoscope. In order to facilitate this dissection, the retroperitoneal 94 and preperitoneal space 96 may be expanded by instilling a pharmaceutically acceptable gas such as $CO_2$, air, an inert gas such as helium or the like. Gas expansion and manual dissection are used to guide the peritoneum toward the midline while separating the lining 94 from the abdominal wall 90. The dissection process continues until there is sufficient room in the retroperitoneal space 96 to access the targeted vertebral body 98 with the surgical apparatus of this invention. During the dissection process care is taken to avoid the ureters 100, iliac vessels, 81 and 82, and the psoas muscles 86. Where this procedure is performed on the upper lumbar vertebrae, care is additionally taken to angle the channel member 40 and the dissecting tools away from the anterior surface of the kidney and associated vessels.

Upon accessing the vertebral body, surgical tools suitable for performing a lumbar discectomy are introduced either through the channel member or directly into the retroperitoneal space, thus permitting the surgeon to perform the discectomy procedure. The channel member additionally includes an endoscope or the like to permit the surgeon to visually guide the surgical apparatus. Similarly, the channel member is capable of being equipped with surgical means, such as a laser fiber or the like, suitable for performing a lumbar discectomy. Irrigation and suction means are also preferably available for use with the channel member. While this invention is described in association with an apparatus similar or identical to the apparatus of this invention, it is contemplated that any number of surgical apparatus may be used that are appropriate for traversing the abdomen of a patient to perform a discectomy while the patient is in a supine position.

A preferred discectomy procedure is described in association with the transperitoneal approach disclosed above. This procedure employs a laser fiber to disassociate disc tissue. While the retroperitoneal lumbar discectomy approach is described in association with FIG. 9 using a channel member device similar to the device of this invention, it is additionally contemplated that any suitable surgical apparatus, as determined by one with skill in the art, could similarly be used. Therefore, the device of this invention should not be construed as a limitation on the surgical methods of this invention. In addition, it is further contemplated that the retroperitoneal approach can be used for a variety of other spinal procedures including lumbar interbody fusions, sympathectomies, and vertebral biopsies.

Advantageously, the retroperitoneal discectomy approach permits the surgeon to reposition a portion of the intact peritoneal cavity including the bowel to access the damaged tissue. Thus, bowel retraction is not a problem. In addition, since the ureter and iliac vessels are closely associated with the peritoneal lining, repositioning of the peritoneum to the midline naturally relocates the ureter and iliac vessels as well. Further, the transperitoneal approach can involve tedious dissections and can, during some procedures, increase the likelihood of postoperative complications. The retroperitoneal approach minimizes these complications. However, both procedures have advantages based on the location of the particular damages disc in need of correction. For example, depending upon location, the retroperitoneal approach can provide easier access to the anterior aspect of the vertebra and the disc space than the transperitoneal approach. Thus, depending on location, a surgeon may select either the transperitoneal or the retroperitoneal as a preferred method for disc surgery. Selection may depend on patient history, the physical attributes of the patient, or the physical location of the particular vertebral body in need of a discectomy. For example, a surgeon may prefer to use the transperitoneal approach for discectomies at the L5-S1 level while preferring the retroperitoneal approach for discectomies involving the L3-L4 and L4-L5 levels.

While particular embodiments of this invention have been described in detail, it will be apparent to those skilled in the art that these embodiments are exemplary rather than limiting, and the true scope of the invention is that defined in the following claims.

What is claimed is:

1. A method of performing a laparoscopic lumbar discectomy comprising:
   creating an incision through the abdominal wall and into the preperitoneal space of a patient;
   dissecting said peritoneal lining from said abdominal wall and instilling a pharmaceutically acceptable gas into said preperitoneal and retroperitoneal space while relocating said peritoneal lining toward the midline of said abdomen thereby expanding said space;
   inserting a surgical apparatus comprising an endoscope and surgical means suitable for performing a lumbar discectomy into said space until said surgical apparatus approaches the anterior aspect of a vertebral body; and
   removing disc tissue utilizing said surgical apparatus.

2. The method of claim 1, wherein said incision is created through said abdominal wall and into the preperitoneal space.

3. The method of claim 2, wherein said incision is lateral to the abdominal midline.

4. The method of claim 3, wherein said incision is adjacent to the abdominal midline.

5. A method of performing a laparoscopic lumbar discectomy comprising:
  creating an expanded retroperitoneal space between the abdominal wall and peritoneal lining by separating said peritoneal lining from said abdominal wall using dissecting means and instilling a pharmaceutically acceptable gas into said retroperitoneal space;
  inserting a surgical apparatus through an abdominal incision into the retroperitoneal space, said surgical apparatus comprising an elongated sleeve member having a first and a second end, endoscope receiving means and an endoscope secured therein, laser fiber receiving means having a laser fiber secured therein, suction and irrigation channel means, each of said means extending along the interior of said sleeve member between said first and second end through said abdominal incision;
  directing said sleeve member into the retroperitoneal space;
  observing the direction of said sleeve using said endoscope;
  guiding said sleeve member through said retroperitoneal space until the second end thereof is adjacent the exterior annulus of a disc space;
  surgically entering the disc space and removing disc tissue by energizing and manipulating said laser fiber;
  directing irrigating fluid through one or more of said conduits; and
  removing fluid with suctioning through one or more of said conduits.

6. The method of claim 5, wherein said abdominal incision is lateral to the abdominal midline.

7. The method of claim 5, wherein said pharmaceutically acceptable gas is $CO_2$.

8. The method of claim 5, wherein said pharmaceutically acceptable gas is air.

9. The method of claim 5, wherein said instilling step is performed prior to or during the guiding step.

10. A method of performing a laparoscopic lumbar discectomy on a patient comprising:
  creating an incision through the abdominal wall and into the preperitoneal space;
  inserting a surgical apparatus comprising an endoscope, irrigation and suction means, and means suitable for performing a lumbar discectomy into said preperitoneal space;
  separating peritoneal ling from the abdominal wall and expanding the retroperitoneal space therebetween;
  traversing said preperitoneal space and said retroperitoneal space toward a lumbar vertebral body with said surgical apparatus until said surgical device approaches the anterior aspect of said vertebral body;
  entering the disk space of said vertebral body; and removing disc tissue utilizing said surgical apparatus.

11. The method of claim 10, wherein said abdominal incision is lateral to the abdominal midline.

12. The method of claim 11, wherein said incision is adjacent said abdominal midline.

13. The method of claim 10, wherein the traversing step additionally comprises the step of instilling a pharmaceutically acceptable gas into said preperitoneal space and said retroperitoneal space thereby expanding said space.

14. A method of performing a laparoscopic lumbar discectomy on a patient comprising:
  creating an incision in the abdominal wall of a patient;
  separating peritoneal lining from the abdominal wall and instilling a pharmaceutically acceptable gas to expand a retroperitoneal space located between said incision and the lumbar vertebrae;
  inserting a surgical apparatus comprising an endoscope and surgical means for performing a lumbar discectomy into said incision;
  directing said surgical apparatus through said expanded retroperitoneal space; and
  removing disc tissue utilizing said surgical apparatus on at lest one vertebral body.

15. The method of claim 14, wherein said incision is adjacent the abdominal midline.

16. The method of claim 14, wherein said pharmaceutically acceptable gas is $CO_2$.

17. The method of claim 14, wherein said pharmaceutically acceptable gas is air.

* * * * *